United States Patent [19]

Nemoshkalov

[11] Patent Number: 5,041,137
[45] Date of Patent: Aug. 20, 1991

[54] METHOD FOR PROSTHETIC RESTORATION OF HUMAN LIMBS

[76] Inventor: Jury I. Nemoshkalov, ulitsa Uralskaya, 190, kv. 152, Krasnodar, U.S.S.R.

[21] Appl. No.: 517,666

[22] Filed: May 1, 1990

[30] Foreign Application Priority Data

Sep. 21, 1988 [SU] U.S.S.R. .............................. 4498475

[51] Int. Cl.$^5$ .............................................. A61F 2/28
[52] U.S. Cl. ......................................... 623/16; 623/27
[58] Field of Search ...................... 623/16, 27, 28, 32, 623/33, 35, 36, 57

[56] References Cited

U.S. PATENT DOCUMENTS

| 3,947,897 | 4/1976 | Owens ................................... 623/27 |
| 4,158,895 | 6/1979 | Reswick et al. ....................... 623/27 |
| 4,547,912 | 10/1985 | Sherva-Parker ....................... 623/16 |

FOREIGN PATENT DOCUMENTS 9003153  4/1990  World Int. Prop. O. ............ 623/16

OTHER PUBLICATIONS

"Constructions of Prosthetic and Orthopedic Devices", 1984, Legkaya Promyshlennost Publishers, pp. 64 and 65.

Primary Examiner—Randy Citrin Shay
Attorney, Agent, or Firm—Fleit, Jacobson, Cohn, Price, Holman & Stern

[57] ABSTRACT

A device for prosthetic restoration of human limbs comprises a supporting member for the stump, shaped as a spherical bowl and connected to the prosthesis of the limb missing portion, and a fixing contrivance interconnecting the stump bone and the supporting member. The supporting member is made of a material indifferent to living tissue and its diameter corresponds to the stump outside diameter. The outer surface of the supporting member is made of a porous material which promotes implantation of living tissue therein, while its top base serves as a support for the stump bone and muscles.

A method for prosthetic restoration of human limbs consists in joining the supporting member to the stump bone, followed by wrapping up of the supporting member by the stump skin, whereupon a suture is applied along the arc of the spherical base of the supporting member; after a period of time has elapsed, necessary for the supporting member to implant, a fistula is established in the spherical base of the member and the latter is connected to the prosthesis of the limb missing portion.

The present invention is applicable, in particular, for prosthetic restoration of the lower and upper limbs of disabled persons, which have been amputated at any level, as well as in cases of vasculopathies and diabetes mellitus.

1 Claim, 3 Drawing Sheets

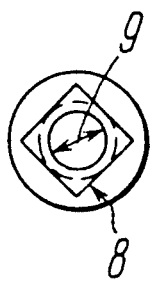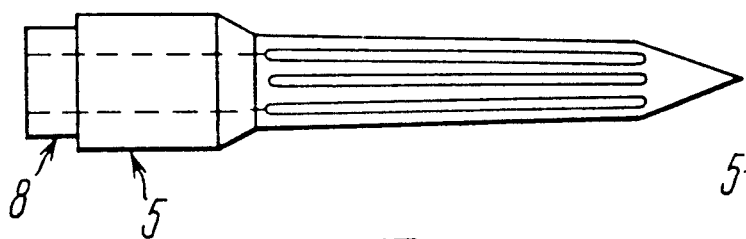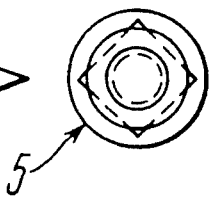
FIG. 5   FIG. 4   FIG. 6
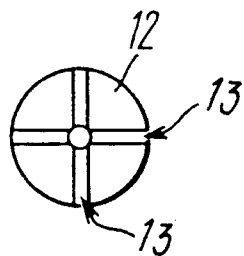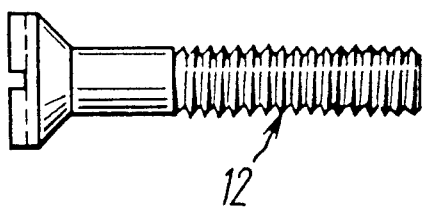
FIG. 8   FIG. 7

METHOD FOR PROSTHETIC RESTORATION OF HUMAN LIMBS

FIELD OF THE INVENTION

The present invention relates generally to medical engineering and has particular reference to a device for prosthetic restoration of human limbs and to a method for such prosthetic restoration.

The invention can find most utility when applied for prosthetic restoration of the lower and upper limbs of disabled persons, which have been amputated at any level, as well as in cases of vascular diseases and diabetes mellitus, wherein poor union of tissues is observed.

BACKGROUND OF THE INVENTION

At present a great majority of disabled persons make use of wooden prostheses of the 1881 model and of leather-and-metallic prostheses of the 1904-1905 pattern (cf. 'Constructions of prosthetic and orthopedic devices', 1984, Legkaya Promyshlennost Publishers, Moscow, pp. 64 and 65 (in Russian). In the recent time prosthetic devices made of modern materials have also been employed.

Known in the present state of the art is a device for prosthetic restoration of human limbs, comprising a supporting member, i.e., a receptacle corset for the stump that makes allowance for the stump size and anatomical shape, and a prosthesis itself aimed at substitution of a limb missing portion and fixed in place in the receptacle corset with the aid of a fixing contrivance.

A method for prosthetic restoration with the aid of the known device discussed above consists in joining the stump to the prosthesis of a limb missing portion through a supporting member, i.e., a receptacle corset adapted to receive the stump.

A substantial disadvantage inherent in both said device and said method resides in the fact that a receptacle corset is used as a supporting member, since firstly it needs strictly individual fitting-up to a patient's stump, which prevents unification of the supporting member, and secondly the stump rests upon the receptacle corset with its lateral surface, which results in disturbance of man's natural supporting scheme.

Moreover, the stump is subjected to compression in the receptacle corset, with the resultant circulation disorders therein, rubbed spots and anebrotic sores.

SUMMARY OF THE INVENTION

It is an object of the present invention to restore the natural support scheme on the skeletal bones to disabled persons.

It is another object of the present invention to provide unification of the proposed device for prosthetic restoration of human limbs.

The foregoing and further objects are accomplished due to the fact that in a device for prosthetic restoration of human limbs, comprising a stump supporting member linked to the prosthesis of the limb missing portion, and a fixing contrivance interconnecting the stump and the supporting member, according to the invention, the supporting member is shaped as a spherical bowl made of a material indifferent to living tissue and having a diameter corresponding to the stump outside diameter, while the fixing contrivance joins the stump bone to the supporting member whose outer surface is made of a porous material, which contributes to implantation of living tissue therein, whereas the top base serves as a support for the bone, muscles, and skin of the stump.

The proposed device enables one to restore patient's natural support scheme on skeletal bones and to avoid injury to the stump. The construction of the supporting member provided with a coating made of a porous material contributing to implantation of living tissue therein, prevents infecting of the stump and renders said member applicable in cases of poor union of tissues, e.g., in the various vasculopathies and in diabetes mellitus. Besides, the invention makes possible industrial-scale production of such devices due to a possibility of their unification, i.e., development of a number of standard sizes in order to suit the stump diameter, as well as the outside and inside diameters of the stump bone.

In a preferred embodiment of the present invention the fixing contrivance is in fact a rod insertable into the medullary canal of the stump bone and joinable with said bone by means of a bonding agent while the tailpiece of said rod has a threaded hole and the supporting member has an open-end hole with a sink and is provided with a screw adapted to pass through the open-end hole into the threaded hole in the rod tailpiece.

Such a construction of the fixing contrivance provides for a reliable linkage between the supporting member and the stump bone and is largely applicable in cases of relatively long stumps.

The foregoing and further objects of the invention are also accomplished due to the fact that in a method for prosthetic restoration of human limbs, consisting in that the stump is joined to the prosthesis of the limb missing portion through a supporting member, according to the invention, used as the supporting member is a spherical bowl, which is joined to the stump bone, whereupon said bowl is wrapped up completely, in the stump skin and a suture is applied along the arc of the bowl spherical base, and after a lapse of time necessary for the bowl to implant, a fistula is established in the bowl spherical base and the bowl is linked to the prosthesis of the limb missing portion.

BRIEF DESCRIPTION OF THE DRAWINGS

Other objects and advantages of the present invention will become clear from the following description of the invention and the accompanying drawings wherein:

FIG. 4 is a rod of the fixing contrivance;

FIG. 5 is the rod of FIG. 4 as seen from its tailpiece;

FIG. 6 is a front view of the rod of FIG. 4;

FIG. 7 is a screw of the fixing contrivance;

FIG. 8 is the screw of FIG. 7 as seen from the tailpiece;

DETAILED DESCRIPTION OF THE INVENTION

Figure 2:
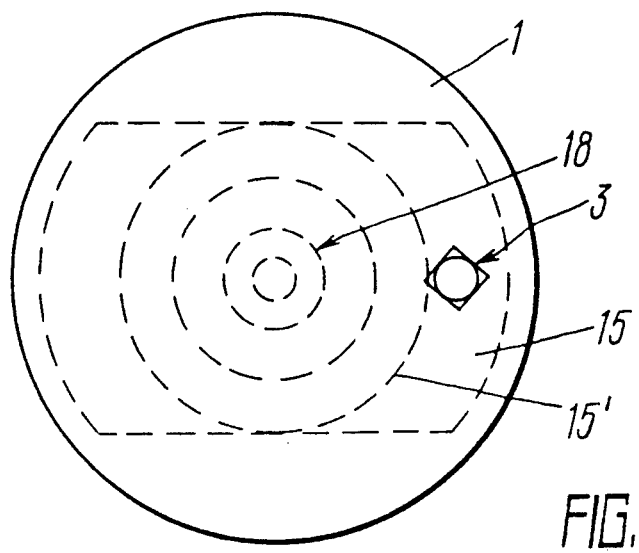
FIG. 2 is a top view of FIG. 1.
Figure 1:
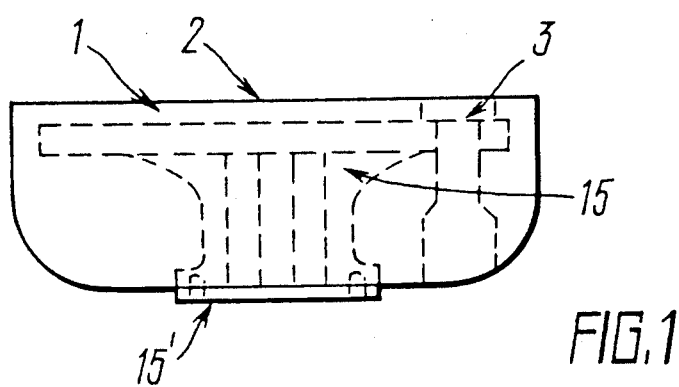
FIG. 1 is a side view of a device, according to the invention.
Figure 3:
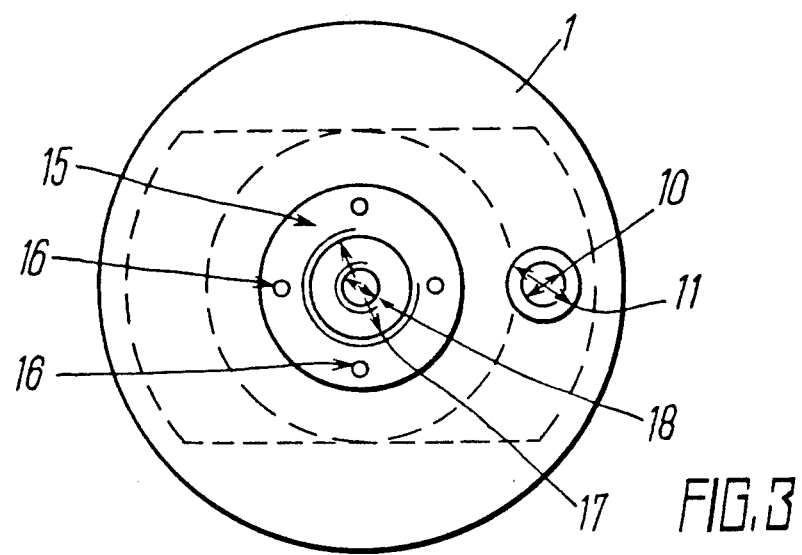
FIG. 3 is a bottom view of FIG. 1.
Figure 9:
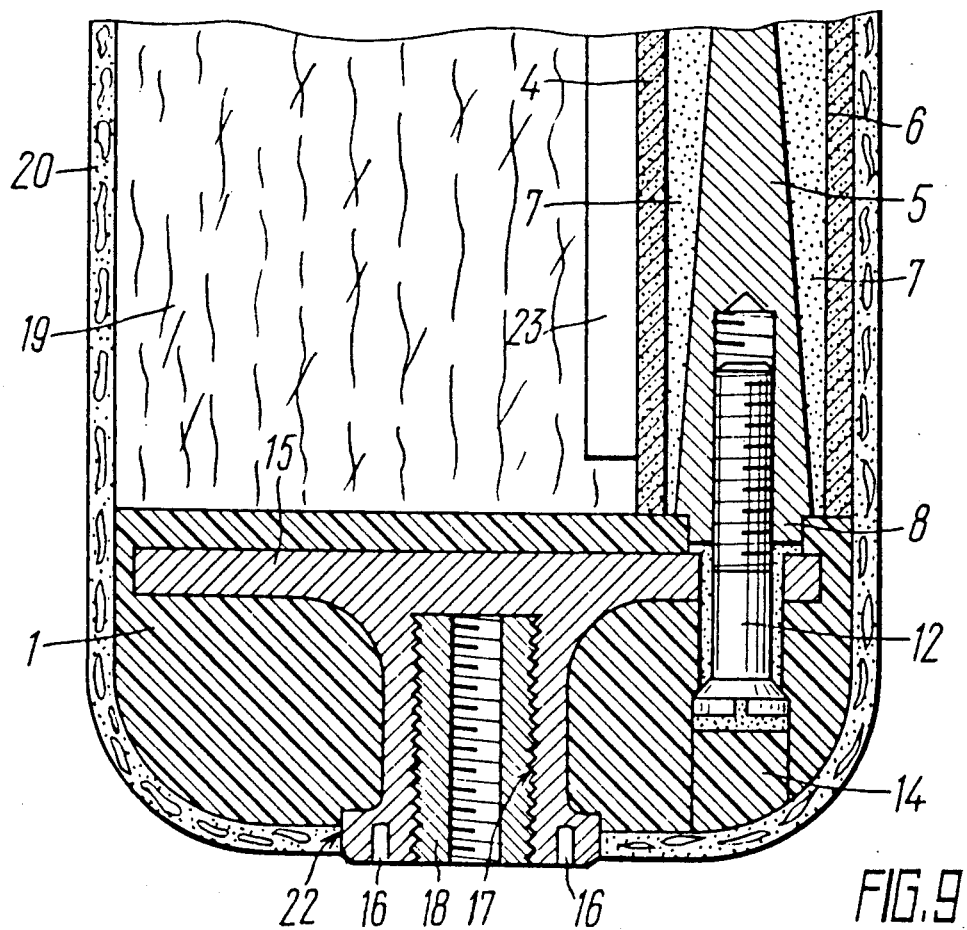
FIG. 9 is a longitudinal sectional view of a supporting bowl as implanted into the stump.

The device for prosthetic restoration of a human limb, i.e., the shin comprises a supporting member 1 (FIGS. 1 through 3) for the stump, said supporting member being shaped as a spherical bowl whose top base 2 has a recess 3 for a bone 4 of the stump to fix therein. A fixing contrivance is provided to interlink the stump bone 4 and the supporting member 1, said contrivance being shaped as a rod 5 (FIGS. 4 through 6) insertable into a medullary canal 6 of the stump bone 4 and joinable to the bone 4 through a binding agent 7 (FIG. 9). The rod 5 is provided with polyhedral tailpiece 8 (FIGS. 4, 5) having a threaded hole 9. The supporting member 1 has an open-end hole 10 (FIG. 3) with a sink 11 and a screw 12 (FIGS. 7, 8) insertable through the hole 10 into the threaded hole 9 in the tailpiece 8 of the rod 5. The head of the screw 12 has slits 13. The sink 11 of the hole 10 accommodates a blank plug 14 (FIG. 9).

A fastener 15 is provided in the supporting member 1 for joining the latter to the prosthesis of the limb missing portion, said fastener being fitted in position in the course of manufacture of the member 1 and fixed in place by pins 16. A bottom base 15' of the fastener 15 extends somewhat from the supporting member 1. The fastener 15 has an axial threaded blind hole 17 to accept a change boss 18 having a male and a female thread and adapted to receive a bolt (omitted in the Drawing) that holds the prosthesis of the limb missing portion.

The method for prosthetic restoration of a human limb, e.g., the shin is carried into effect as follows.

Soft tissues 19 (FIG. 9) at the stump end are cut open to expose the bone 4, whereupon a skin 20 is everted onto the stump, and the bone 4 is reamputated for a length slightly exceeding the height of the supporting member 1 so that the front flap of the skin 20, when a suture 21 is being applied, overlaps the bottom base 15' of the fastener 15 by at least one centimeter, which is necessary in order that a fistula 22 be afterward established in an intact skin area.

Then the soft tissue 19 is cut off at the level of the reamputated bone 4, the medullary canal thereof is cleaned and an agent is introduced into said canal that is capable to establish a firm union between the rod 5 inserted into the medullary canal of the bone 4 along with said agent, and the bone 4. Used as such an agent may be, e.g., acrylic-resin cement. In 5 to 7 minutes the supporting member 1 is held to the bone 4 through the screw 12, which is turned through the hole 10 into the hole 9 in the rod 5. Then the blank plug 14 is fitted into the sink 11 of the hole 10.

Figure 10:
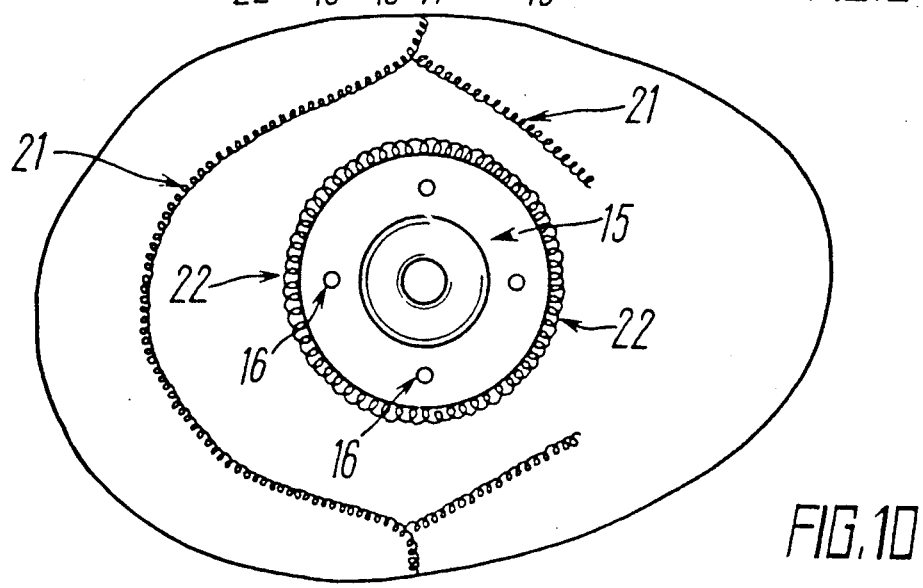
FIG. 10 is a bottom view of the supporting bowl of FIG. 9.

Next the front and rear flaps of the skin 20 are cut off to acquire the required configuration so that the suture 21 (FIG. 10) be applied along the arc of a spherical surface of the supporting member 1 at least one centimeter apart from the edge of the fastener 15.

Thereupon old sutural cicatrices are cut off and an active drainage is established. The implanting time of the supporting member 1 is from 4 to 6 weeks, whereupon the fistula 22 is formed around the fastener 15. The bottom base 15' of the fastener 15 gets exposed and, once the fistula 22 has healed up, the prosthesis of the limb missing portion can be held to the fastener 15.

Then a fibula 23 is reamputated so as to get 1 to 2 cm shorter than the tibia 4 and is not engaged in the prosthetic restoration as being of low efficacy as a bearing bone.

The supporting member 1 may be made of porous materials indifferent to living tissue and possessing adequate strength and low heat conductivity. In the inventor's opinion a polymer material, viz., a carbon-fibre reinforced plastic is most suitable for the supporting member 1.

The supporting member 1 gets implanted due to the fact that the pores of the porous material are grown-in by the osteons of the spongy osseous tissue and by the fibres of the soft tissue, which is to be fostered by appropriately selected size of pores, that is, 10 to 500 $\mu m$ and by prefilling said pores with an agent establishing biological compatibility of endoprosthetic materials.

The recess 3 is to be established in the course of manufacture of the supporting member 1 so as to suit, as for shape and size, the shape and size of the tailpiece 8 of the rod 5. The dimensions of the rod 5 are selected so as to suit the dimensions of the medullary canal 6 of the bone 4 as shown on X-ray pictures taken in the various projections within the preparatory period.

Subsequent unification of the supporting member is practicable due to the provision of a number of standard sizes thereof.

The screw 12 and the rod 5 are to be made of a stainless metal, as well as the fastener 15, which is inserted into the supporting member 1 in the course of manufacture of the latter.

The change threaded boss 18 is made of stainless steel amenable to heat treatment.

What is claimed is:

1. A method for prosthetic restoration of a human limb having a stump, consisting in joining a supporting member shaped as a spherical bowl, to a stump bone, said supporting member being made of a material indifferent to living tissue, while its diameter corresponds to the outside diameter of said stump; said supporting member having a coating made of a porous material, which promotes implantation of living tissue therein, and a top base of said supporting member serving as a support for bone and muscles of said stump; once said joining of said stump bone and said supporting member has been carried out, said supporting member is wrapped up completely in skin of the stump and a suture is applied along an arc of the spherical bowl of said supporting member, and after a period of time has elapsed, necessary for said supporting member to implant, a fistula is established in the skin of the stump within a zone of the spherical bowl of the supporting member to expose connection means of said supporting member and said connection means is connected to a prosthesis of a missing limb portion.

* * * * *